United States Patent [19]

Laurent et al.

[11] 4,456,620

[45] Jun. 26, 1984

[54] D-HOMO-4,17-ANDROSTADIEN-3-ONE, ITS PREPARATION AND PHARMACEUTICAL USE

[75] Inventors: Henry Laurent; Rudolf Wiechert, both of Berlin, Fed. Rep. of Germany

[73] Assignee: Schering Aktiengesellschaft, Berlin and Bergkamen, Fed. Rep. of Germany

[21] Appl. No.: 367,866

[22] Filed: Apr. 13, 1982

[30] Foreign Application Priority Data

Apr. 13, 1981 [DE] Fed. Rep. of Germany ....... 3115995

[51] Int. Cl.³ .......................................... A01N 35/00
[52] U.S. Cl. .................................... 424/331; 568/326
[58] Field of Search ....................... 424/331; 568/326

[56] References Cited

U.S. PATENT DOCUMENTS 3,492,338  1/1976  Hader et al. ................... 424/331
3,984,476 10/1976  Furst et al. .................... 424/331

OTHER PUBLICATIONS

CA-vol. 68 (1968), No. 13, par. 59.797x, Abstract of an article by Stork et al., "J. Amer. Chem. Soc.", vol. 89(21), 5464–5465, (1967).

Primary Examiner—Elbert L. Roberts
Attorney, Agent, or Firm—Millen & White

[57] ABSTRACT

D-Homo-4,17-androstadien-3-one is a pharmacologically effective compound having antiandrogenic activity upon topical application. The compound can be prepared from D-homo-5,17-androstadien-3β-ol by oxidation with simultaneous isomerization of the 5(6)-double bond.

1 Claim, No Drawings

D-HOMO-4,17-ANDROSTADIEN-3-ONE, ITS PREPARATION AND PHARMACEUTICAL USE

BACKGROUND OF THE INVENTION

The present invention relates to D-homo-4,17-androstadien-3-one, a process for its production, and pharmaceutical preparations containing it.

4,16-Androstadien-3-one is a compound which has been known for some time. It is formed during the metabolizing of other steroids, for example testosterone [J. Biol. Chem. 236:692 (1961)] or dehydroepiandrosterone [Steriods 8:511 (1966)]. Yet, this compound nas never been investigated in greater detail pharmacologically, obviously because it has a pronounced "urine odor" [Helv. Chim. Acta 28:618 (1945)], rendering it unsuitable as an active ingredient in medicines.

It is known that derivatives of 4,16-androstadien-3-one have an antiandrogenic effect upon local application (DOS No. 2,631,915 and South African Pat. No. 79.01974). However, these compounds have the drawback that their effectiveness is relatively low, or that they additionally cause undesirable systemic antiandrogenic effects. Moreover, known compounds of a less analogous structure and not burdened by these disadvantages, unfortunately have an intense "urine odor" as determined by in-house experiments described hereinbelow.

SUMMARY OF THE INVENTION

Accordingly, it is an object of this invention to provide new pharmacologically active agents having valuable properties and being free of the mentioned disadvantages or possessing them to a significantly lesser degree.

Upon further study of the specification and appended claims, further objects and advantages of this invention will become apparent to those skilled in the art.

These objects have been attained based on the finding that D-homo-4,17-androstadien-3-one possesses a pronounced topical antiandrogenic activity, greatly inhibits lipogenesis, and, furthermore, has the advantage that it is systemically ineffective and entirely odorless. These facts have been demonstrated by the test results shown below.

DETAILED DISCUSSION

The antiandrogenic activity can be determined by conventional protocols, for example, the following method can be used.

Male, fertile hamsters weighing around 80 g are castrated and subcutaneously substituted daily with 0.1 mg of testosterone propionate. The right ear is treated twice daily with 0.01 ml of a 3% solution of the test compound in acetone or ethanol for a period of three weeks. In the control group, the right ear is treated merely with 0.01 ml of solvent.

On the 22nd day, the animals are sacrificed with ether; prostate and seminal vesicle are prepared and weighed. Respectively defined tissue areas having an edge length of 3×7 mm are punched out from the ears; these are further processed histologically, and the areas of the sebaceous glands are measured. By comparing the areas of the ventral side of the ears of the animals treated with the antiandrogen with the same regions in the animals treated merely with solvent, a measure is obtained of the local antiandrogenic effect of the test compound. The reduction in weight of prostate and weight of seminal vesicle observed in comparison with a control group demonstrates the extent of the systemic antiandrogenic activity of the test compound.

The effect of the test compounds on the lipogenesis can be determined by conventional protocols, e.g., as follows:

Male, fertile hamsters weighing about 80-100 g are castrated and substituted subcutaneously daily with 0.1 mg of testosterone propionate. The right ear of each test animal is treated twice daily with 0.01 ml of a 1% solution of the test compound in actone (in the case of the control group, only with 0.01 ml of solvent) for a period of three weeks. The animals are then sacrificed. A defined tissue area of a diameter of 8 mm is punched out from the treated right ear of each as well as from the untreated left ear.

The ventral and dorsal sides of the punched-out sections are separated from each other along the ear cartilage, immediately transferred into Dulbecco's modification of Eagle's medium, to which had been added 4 mmol of glutamine and 10% calf serum, and, to avoid microbial contamination, which also contained 100 IU/ml of penicillin, 100 $\mu$g/ml of streptomycin, 125 $\mu$g/ml of kanamycin, 25 IU/ml of nystatin, and 10 $\mu$g/ml of gentamycin. They are incubated at 37° C. for one hour.

Thereafter, the punched-out sections and introduced under aseptic conditions into fresh culture medium containing 1 $\mu$Ci/ml of $C^{14}$-labeled sodium acetate, and incubated at 37° C. for 4 hours. The specimens are then introduced into 2 ml of a proteolysis solution made up of 0.05 mole of tris buffer having a pH of 7.5, 0.01 mole of disodium ethylenediaminetetraacetic acid, 0.5% of sodium dodecyl sulfate, and 0.1% of proteinase K (E. Merck A. G., Darmstadt, Federal Republic of Germany). The mixture is incubated for 24 hours at 37° C.

The thus-obtained specimens are extracted once with 5 ml of chloroform and once more with 3 ml of chloroform; the combined chloroform extracts are concentrated under vacuum, and the content of radiolabeled lipids in the extracts is determined by a scintillation counter. The percent inhibition of the lipogenesis of the treated group is calculated by comparison with the control group treated solely with solvent.

The following table shows the results obtained in these tests.

TABLE

| No. | Compound | Area Reduction of Sebaceous Glands | | Weight Reduction | | Change in Lipogenesis | | Urine Odor |
| | | Treated Ear | Contra-lateral Ear | Prostate | Seminal Vesicle | Treated Ear | Contra-lateral Ear | |
| --- | --- | --- | --- | --- | --- | --- | --- | --- |
| 1 | 4,15-Estradien-3-one | 74% | 44% | 0% | 0% | −28% | −8% | Very Strong |
| 2 | 18-Methyl-4,16-estradien-3-one | 62% | 18% | 15% | 10% | −37% | −7% | Strong |

TABLE-continued

| | | Area Reduction of Sebaceous Glands | | Weight Reduction | | Change in Lipogenesis | | |
|---|---|---|---|---|---|---|---|---|
| No. | Compound | Treated Ear | Contra-lateral Ear | Prostate | Seminal Vesicle | Treated Ear | Contra-lateral Ear | Urine Odor |
| 3 | D-Homo-4,17-androstadien-3-one | 67% | 24% | 0% | 0% | −30% | −12% | Odorless |

For topical application, D-homo-4,17-androstadien-3-one can be processed together with the conventional excipients into solutions, gels, ointments, powders, or other preparations. Suitable excipients include, for example, water, ethanol, propanol, glycerin, methylcellulose, hydroxypropylcellulose, carboxypolymethylene, etc. The antiandrogen is preferably present in a concentration of 0.05–5.0% by weight, based on the total weight of the preparation. The preparations can be utilized for the topical treatment of diseases such as acne, seborrhea, alopecia, and hirsutism. They can be administered analogously to the known topical agent cypoterone acetat.

D-Homo-4,17-androstadien-3-one can be prepared by oxidizing D-homo-5,17-androstadien-3$\beta$-ol with simultaneous isomerization of the 5(6)-double bond, for example under the conditions of the so-called Oppenauer oxidation (Carl Djerassi: Steroid Reactions, Holden-Day, Inc., San Francisco, 1963, pages 89 et seq., whose disclosure is incorporated by reference herein). The starting material can be prepared, e.g., as shown in the example below, from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE (A) A solution of 10.0 g of 3$\beta$-acetoxy-D-homo-5-androsten-17a-one in 350 ml of methanol is combined with 20 g of p-toluenesulfonic acid hydrazide and heated to boiling after the addition of 0.5 ml of concentrated sulfuric acid. After 30 minutes, the solution is cooled and stirred into ice water. The precipitate is filtered off, washed with water, and dried. Yield: 14.0 g of 3$\beta$-acetoxy-17a-p-toluenesulfonylhydrazono-D-homo-5-androstene.

(B) A solution of 14.0 g of 3$\beta$-acetoxy-17a-p-toluenesulfonylhydrazono-D-homo-5-androstene in 280 ml of tetrahydrofuran is cooled to 0° C. and combined with 140 ml of a 1.3-molar ethereal methyllithium solution. The reaction mixture is allowed to stand for 24 hours at 4° C., then diluted with 300 ml of ether, washed with water, dried over sodium sulfate, and concentrated under vacuum. The residue is chromatographed on silica gel, thus obtaining by elution with a hexane-ethyl acetate gradient (17–23% ethyl acetate) 7.82 g of D-homo-5,17-androstadien-3$\beta$-ol, mp 138° C. (from hexane-acetone).

(C) A solution of 675 mg of aluminum isopropylate in 14 ml of toluene is added to a solution of 2.7 g of D-homo-5,17-androstadien-3$\beta$-ol in 40 ml of toluene and 14 ml of cyclohexanone. The reaction mixture is heated to boiling for one hour, then cooled, combined with 50 ml of water, and extracted with dichloromethane. The extract is subjected to steam distillation and the resultant residue is extracted with dichloromethane. The organic phase is dried over sodium sulfate and concentrated. The thus-obtained crude product is chromatographed on silica gel, yielding with a hexane-ethyl acetate gradient (10–14% ethyl acetate) 1.86 g of D-homo-5,17-androstadien-3-one, mp 123° C. (from acetone-hexane).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating acne, seborrhea, alopecia or hirsutism in a patient comprising administering an antiandrogenically effective amount of a topically administerable pharmaceutical composition comprising an antiandrogenically effective amount of D-homo-4,17-androstadien-3-one and a pharmaceutically acceptable carrier which is suitable for topical administration, and wherein the concentration of D-homo-4,17-androstadien-3-one is 0.5–5.0 wt. %.

* * * * *